United States Patent [19]

Tararine et al.

[11] Patent Number: 5,373,161
[45] Date of Patent: Dec. 13, 1994

[54] GAMMA CAMERA WITH GAIN COMPENSATION

[75] Inventors: Michel Tararine, Asnieres; Jean-Francois Benard, Longjumeau, both of France

[73] Assignee: Sopha Medical, Buc Cedex, France

[21] Appl. No.: 186,588

[22] Filed: Jan. 26, 1994

[30] Foreign Application Priority Data

Jan. 27, 1993 [FR] France ............... 93 00805

[51] Int. Cl.⁵ ............................................. G01T 1/208
[52] U.S. Cl. ............................ 250/363.09; 250/252.1; 250/369
[58] Field of Search ............. 250/363.07, 363.09, 250/369, 252.1 A, 252.1 R

[56] References Cited

U.S. PATENT DOCUMENTS

| | | | |
|---|---|---|---|
| 3,980,886 | 9/1976 | Stout | 250/369 |
| 4,475,042 | 10/1984 | Arseneau | 250/363 |
| 4,629,895 | 12/1986 | Mestais et al. | 250/369 |
| 4,866,615 | 9/1989 | Ichihara | 364/413.24 |
| 5,004,904 | 4/1991 | Yamakawa et al. | 250/363.09 |
| 5,237,173 | 8/1993 | Stark et al. | 250/363.09 |

*Primary Examiner*—Carolyn E. Fields
*Attorney, Agent, or Firm*—Kerkam, Stowell, Kondracki & Clarke

[57] ABSTRACT

A gamma camera includes means for the localization of scintillations produced under the effect of a gamma radiation in a scintillator crystal, the localization means including an array of photomultiplier tubes with gain control obtained by means of calibrated light pulses, and a localization circuit wherein each photomultiplier tube is connected, firstly, through a diode called a resolution diode, to a weighting circuit comprising a network of resistors connected to output adders and, secondly, to a linearizing circuit giving a signal called a linearity signal. The linearizing circuit also gives, for a duration at least equal to the duration of the calibrated light pulses, a pulse to inhibit the resolution diode with respect to the electrical pulses delivered by the photomultiplier tube in response to the light pulses.

1 Claim, 1 Drawing Sheet

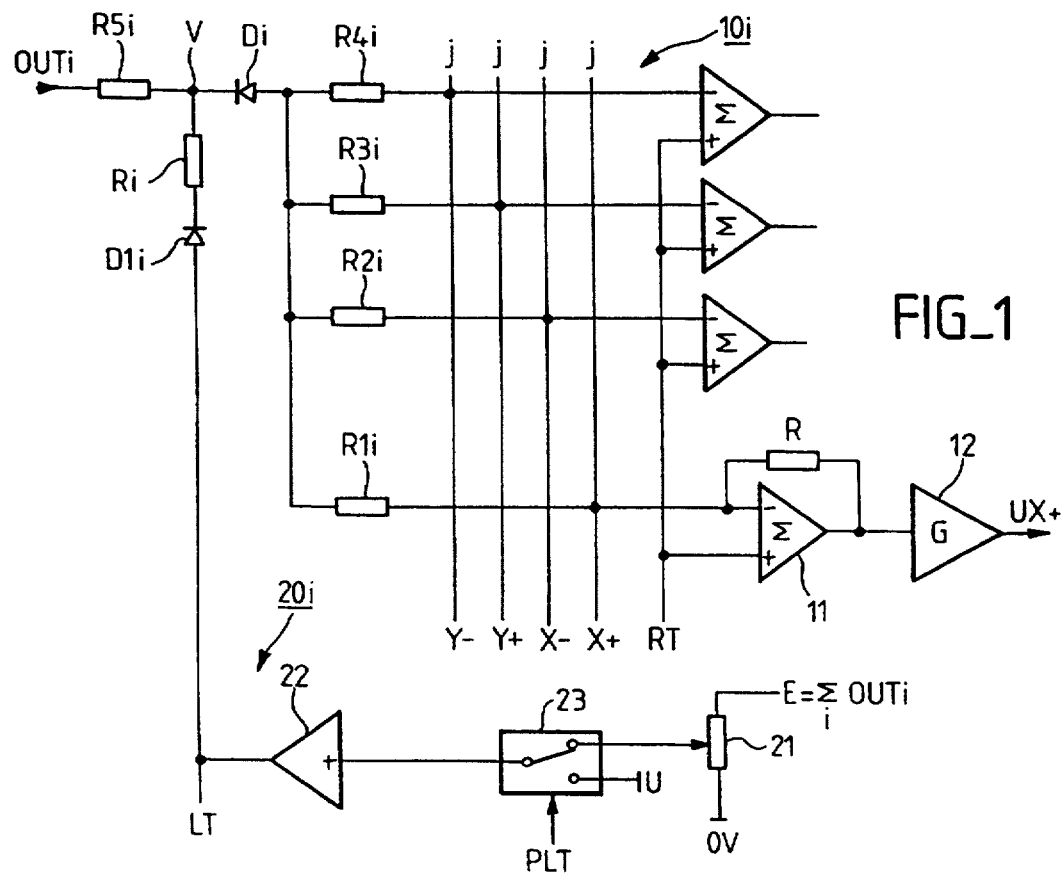
FIG_1
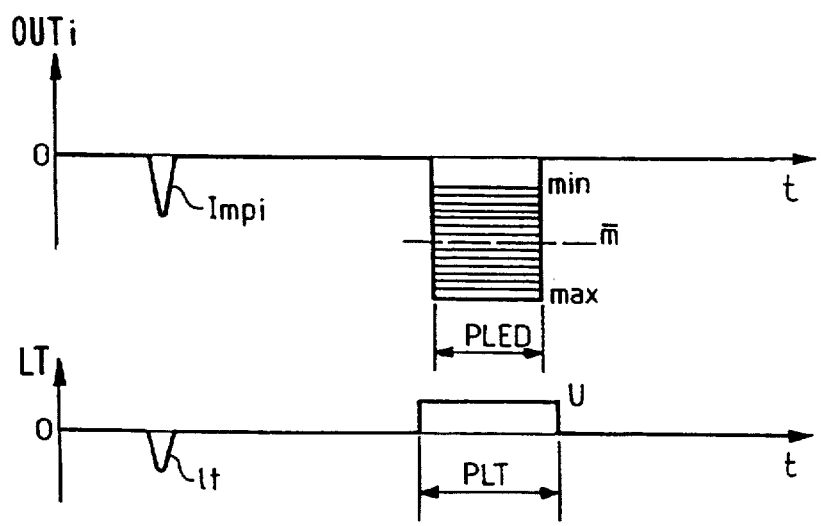
FIG_2a
FIG_2b

GAMMA CAMERA WITH GAIN COMPENSATION

BACKGROUND OF THE INVENTION

1. Field of the Invention

The present invention relates to a gamma camera comprising means to localize the scintillations produced under the effect of a gamma radiation in a crystal scintillator.

The invention can be applied in a particularly advantageous way in the field of nuclear medicine for the display, in an organ, of the distribution of molecules marked by a radioactive isotope that has been injected into a patient.

2. Description of the Prior Art

There is, for example, a known gamma camera described in the U.S. Pat. No. 4,629,895. This known gamma camera, in accordance with the preamble, comprises a collimator to focus the gamma photons emitted by the patient, a scintillator crystal to convert the gamma photons into light photons or scintillations and an array of photomultiplier tubes which, in turn, convert the received scintillations into electrical pulses. This array of photomultiplier tubes forms part of localization means that use electrical pulses given by the tubes to deliver, in a known way, X and Y coordinate signals of the position at which the scintillation has taken place, as well as a validation signal when the energy E of the scintillation belongs to a predetermined energy band.

Since the scintillation is perceived by several photomultiplier tubes simultaneously, the location of this scintillation on the crystal, which itself represents the place of emission of the excitation gamma photon, is determined by computing the location of the barycenter of the electrical pulses delivered by all the photomultiplier tubes excited by the scintillation considered. This computation is done simply, according to the above-mentioned U.S. patent, by connecting each photomultiplier tube, through a diode called a resolution diode, to a weighting circuit comprising a matrix of resistors and output adders. The resistance values of the resistors of the matrix are a function of the positions of the photomultiplier tubes to which it is connected. These resolution diodes D have the function of giving a non-linear response to the circuits for the preamplification of the output signals of the photomultiplier tubes, by the addition of a threshold effect.

The output signal of a given photomultiplier tube will be transmitted through the resolution diode D only if it is greater in terms of absolute value than $S^D - RT$ where:

$S^D$ is the conduction threshold of the diode D, for example 0.6 V for a silicon type diode;

RT is a constant potential applied to the diode D, designed to fix the threshold value of the threshold at a determined level.

This threshold effect improves the spatial resolution, whence the term "resolution threshold", and is described in the article by G. H. Kerberg and N. Van Dijk, "Improved Resolution Of The Anger Scintillation Camera Through The Use of Threshold Preamplifiers" in *Journal of Nuclear Medicine*, 13, pp. 169–171, 1972.

Furthermore, each of the photomultiplier tubes is connected to a linearizing circuit giving a linearity threshold synchronously with the electrical pulse coming from the corresponding photomultiplier tube.

This linearity threshold has the function of attenuating the output signal of the photomultiplier tube or tubes giving the highest signal during an event. Indeed, the barycenter of the electrical pulses delivered by all the photomultiplier tubes following a scintillation is only an estimator of the location of this scintillation on the crystal. This estimator comprises a systematic error element, called a "bias", and this bias is the chief source of the intrinsic spatial distortions of the gamma camera.

One way to minimize this bias is to attenuate the output signal of the photomultiplier tube or tubes that face the scintillation and that consequently give the highest signal. In practice, this operation can easily be carried out by routing or shunting the output signal of each photomultiplier tube by using a diode that is reverse-biased by means of a pulse signal proportional to the total energy of the event, this pulse signal being called a "linearity threshold" signal. Thus, during a scintillation, the photomultiplier tubes giving a signal with an amplitude higher than the linearity threshold will have their output signal attenuated by the routing of the current through the diode whose junction gets turned on.

The photomultiplier tubes have nevertheless the drawback wherein their gain is likely to undergo drifts in the course of time owing, notably, to changes in the characteristics of the photoemissive materials or secondary emission materials used, the ageing of the electronic processing circuits, and the sensitivity of the tubes to the magnetic field. This variation of the gain of the photomultiplier tube results in a notable loss of information. Indeed, firstly, it is possible that electrical pulses which should normally have been taken into account may not be validated owing to the fact that an energy E of scintillation is apparently outside the window of analysis and, secondly, these gain variations modify the signals used to compute the location of the barycenter of the scintillation and therefore introduce spatial distortions that lower the quality of the images obtained.

To overcome this drawback, it is possible to resort to a prior calibration of the photomultiplier tubes. However, this procedure is not satisfactory for it takes a great deal of time (from one to two hours) to implement, does not take the ageing of the electronic circuitry into account and is valid only for a given position of the gamma camera with respect to the surrounding magnetic field.

Other, more advantageous approaches consist of a permanent compensation for the drift in the gain of the photomultiplier tubes. Among the most frequently used methods, we may cite calibration by nuclear spectrometry which relies on the fact that the position of a photoelectrical absorption peak of an energy spectrum of a given radioisotope depends on the gain of the tubes. In this method, a recording is made for example of a nuclear spectrum during the clinical acquisition, the gain of these photomultiplier tubes being adjusted so as to maintain the position of the emission peak within a given window of energy values. This known calibration technique, however, is not without its limits. Indeed, it will be seen that it cannot be used with any radio-element whatsoever. In particular, radio-elements that show far too many peaks have to be excluded. Furthermore, this type of calibration cannot take account of the fact that the shape of the spectra depends on the configuration of the patient, for the diffusion of the gamma photons differs according to the patient's degree of corpulence. Finally, the photomultiplier tubes are not illuminated homogeneously so that, during the clinical examination when the activity is concentrated in a small zone, it is only the tubes facing this zone (this zone being therefore the one in which the events occur) that are corrected in terms of gain and not the other tubes whereas these other tubes make as much of a contribution to the localization of the scintillation. The result of this, therefore, is an error. Similarly, the photomultiplier tubes at the edge of the field can never be adjusted for, owing to the presence of the collimator, they never receive direct light.

Another method of calibrating photomultiplier tubes in terms of gain consists in using external light sources such as light-emitting diodes to illuminate each tube with a known quantity of light and to modify the gain thereof accordingly when the tube response varies in the course of time.

Practically speaking, the light-emitting diodes can be placed in the very interior of the photomultiplier tubes or again outside the tubes, it being possible for a diode to simultaneously illuminate several tubes, for example three tubes in the case of an array of hexagonal tubes. During the clinical examination, the light sources emit calibrated pulses having a determined duration, for example a duration of 1 to 2 µs, in emitting these pulses with a given frequency, for example every millisecond. The compensation for the gain is done in real time successively or simultaneously for all the photomultiplier tubes, after the accumulation, over a sufficient duration of the spectrum, of the electrical pulses given in response to the light pulses received. The gain of the tubes may be adjusted by means of a variable gain preamplifier controlled by an appropriate software program and a digital/analog converter.

It must be noted, however, that the amplitude of the electrical calibration pulses is such that, after summation on all the tubes by the output adders, there is a substantial saturation of the localization circuits that results in a relatively lengthy recovery time of the order of 10 µs. Consequently, the detection of the nuclear events is disturbed during the recovery period, unless the circuit-inhibition time is increased to 10 µs at least, which would lead to a substantial diminishing of the counting rate.

SUMMARY OF THE INVENTION

Thus, the technical problem to be resolved by the object of the present invention is that of proposing a gamma camera comprising means for the localization of scintillations produced under the effect of a gamma radiation in a scintillator crystal, said localization means comprising an array of photomultiplier tubes with gain control obtained by means of calibrated light pulses, and a localization circuit wherein each photomultiplier tube is connected, firstly, through a diode called a resolution diode, to a weighting circuit comprising a network of resistors connected to output adders and, secondly, to a linearizing circuit giving a signal called a linearity signal, said gamma camera making it possible to avoid the drawbacks related to the time taken by the circuits to recover from saturation following the optical calibration of the tubes, without any substantial diminishing of the rate of counting of the scintillations.

In the solution, according to the present invention, of the technical problem posed, said linearizing circuit comprises means also to give, for a duration at least equal to the duration of the calibrated light pulses, a pulse to inhibit said resolution diode with respect to the electrical pulses delivered by the photomultiplier tube in response to said light pulses.

Thus, said inhibition pulse, constituted by a reverse biasing of the resolution diode, enables a reduction of the current injected into the matrix of resistors by the set of photomultiplier tubes and makes it possible to avoid the saturation of the localization channels. The period of time during which the nuclear events are not accessible is thus reduced to the duration of the inhibition pulse, for example 2.5 µs instead of 10 µs, giving a gain by a factor of four as compared with the period of time during which the localization circuit devoted to the calibration of the tubes is kept occupied.

BRIEF DESCRIPTION OF THE DRAWINGS

The following description, made with reference to the appended drawings, which are given by way of non-restrictive examples, will provide a clear understanding of the content of the invention and the way in which it can be achieved.

FIG. 1 is a diagram of a partial circuit for the localization of a gamma camera according to the invention, limited to only one photomultiplier tube;

FIG. 2a is a timing diagram of the output signal of the photomultiplier tube according to figure 1;

FIG. 2b is a timing diagram of the threshold of linearity applied to the tube of FIG. 1 and corresponding to the timing diagram of FIG. 2a.

MORE DETAILED DESCRIPTION

FIG. 1 shows a schematic view of a partial localization circuit, pertaining to a photomultiplier tube represented by the index i. The tube i and the associated partial localization circuit form part of means for the localization of scintillations produced in a gamma camera under the effect of a gamma radiation in a scintillator crystal. These localization means comprise an array of photomultiplier tubes, the number of which is 58 for example (i=1, 2 . . . , 58), and a localization circuit formed by 58 partial circuits of the type shown in FIG. 1.

The circuit of FIG. 1 comprises a weighting circuit $10i$ to which the output OUTi of the photomultiplier tube i is connected through a resistor R5$i$ and a diode Di called a resolution diode. This weighting circuit comprises a network of resistors R1$i$, R2$i$, R3$i$, R4$i$ whose values are determined in a known way to define the weighted pulses X+, X−, Y+, Y− given by:

$$X+ = \sum_i (R/R1i) \times \text{OUT}i \quad X- = \sum_i (R/R2i) \times \text{OUT}i$$

$$Y+ = \sum_i (R/R3i) \times \text{OUT}i \quad Y- = \sum_i (R/R4i) \times \text{OUT}i$$

The summation operations are carried out on all the photomultiplier tubes of the gamma camera by four adder circuits such as the one referenced 11 corresponding to the weighted pulse X+. To these adder circuits there are connected all the weighting circuits associated with the set of photomultiplier tubes, namely the tube i considered herein and the other tubes indexed j which are different from i. The signals coming from all the tubes are applied to the negative terminals of the adders while their positive terminals are taken to a potential, called a resolution threshold RT, equal to 0.2 V for example. The X and Y coordinates of the detected scintillation are defined by:

$$X = \frac{X+ - X-}{X+ + X-} \quad Y = \frac{Y+ - Y-}{Y+ + Y-}$$

The output of the photomultiplier tube i is also connected, again through the resistor R5i, to a linearizing circuit 20i in which a linearity threshold LT, given by a circuit comprising a potentiometer 21 receiving the energy signal E and an amplifier 22, is applied to a diode D1i, called a linearity diode, in series with a resistor Ri.

When, as indicated in FIGS. 2a and 2b, the photomultiplier tube i delivers an electrical pulse Impi at its output OUTi in response to a light scintillation produced following a gamma emission from the radio-element injected into the patient, a linearity threshold lt is applied synchronously to the input of the linearity diode D1i. The electrical pulse Impi may typically reach a peak value of $-3$ V, while the linearity threshold It is placed around $-0.2$ V peak.

The photomultiplier tubes of the gamma camera according to the invention are provided with gain compensation by means of calibrated light pulses emitted at a given frequency of recurrence, for example 1 kHz, i.e. once every millisecond. These light pulses may be given by light-emitting diodes positioned so as to be adjacent to three hexagonal photomultiplier tubes which are placed so as to be the closest neighbors of one another. According to FIG. 2a, the light intensity emitted by the calibration light-emitting diodes is such that the corresponding electrical pulse delivered by the photomultiplier tubes may vary between a minimum value Min equal to $-2$ V and a maximum value Max equal to $-9$ V with a mean value m of $-5.5$ V, the duration PLED of this pulse being of the order of 1.75 µs for example.

If, during the application of the light pulses, the linearity threshold LT were to be kept at 0 V, the voltage V at output of the resistor R5i, which is expressed by the general relationship:

$$V = (LT - 0.6) + (OUTi - LT + 0.6) \times \frac{Ri}{Ri + R5i}$$

would be equal to $-1.8$ V with LT=0, OUTi=m=$-5.5$ V, Ri=422 Ω and R5i=1.3 kΩ. The value of 0.6 V corresponds to the reverse bias voltage of the diode D1i.

The voltage UX+ delivered by the amplifier 12 with a gain G after addition by the adder 11 of the signals coming from the N photomultiplier tubes is given by:

$$UX+ = -N \times \frac{R}{R1i} \times G \times (V + 0.4)$$

With N=58, R=2 KΩ; R1i mean=15 KΩ and G=5.2, we get:

$$UX+ = +56 \text{ V}$$

which indicates a substantial saturation of the output amplifier, implying a post-saturation recovery time that may go up to 10 µs, a period of time during which events, although deformed, are nevertheless taken into account. This results in errors in the localization of the scintillations and, therefore, in a disturbance of the image given by the gamma camera.

It may be noted that, in reality, the saturation would be even greater because the linearity threshold LT comes from the voltage source E, which is saturated during the light pulses and is hence highly negative, whence a value of V equal to $-5.5$ V, the diodes D1i being inhibited.

Conversely if, during a period PLT at least equal to the duration PLED of the calibration light pulses, equal to 2.5 µs for example, a inhibition threshold of linearity LT, equal to U=$+2$ V, is applied by operating an electronic change-over switch 23 at the above-mentioned frequency of recurrence, we get:

$$V = -0.29 \text{ V}$$

The resolution diodes Di are therefore inhibited and UX+ =0. The output amplifier is then no longer saturated, thus eliminating the harmful effects related to recovery after saturation.

In practice, there is a slight conduction current in the diodes which gives a signal UX+ ≦5 V, the output amplifier being no longer saturated.

Naturally, the reasoning formulated herein with respect to the X+ coordinate is also valid for the X−, Y+ and Y− coordinates.

What is claimed is:

1. A gamma camera comprising means for the localization of scintillations produced under the effect of a gamma radiation in a scintillator crystal, said localization means comprising an array of photomultiplier tubes with gain control obtained by means of calibrated light pulses, and a localization circuit wherein each photomultiplier tube is connected, firstly, through a diode called a resolution diode, to a weighting circuit comprising a network of resistors connected to output adders and, secondly, to a linearizing circuit giving a signal called a linearity signal, wherein said linearizing circuit comprises means also to give, for a duration at least equal to the duration of the calibrated light pulses, a pulse to inhibit said resolution diode with respect to the electrical pulses delivered by the photomultiplier tube in response to said light pulses.

* * * * *